United States Patent [19]

Diel et al.

[11] Patent Number: 4,739,093

[45] Date of Patent: Apr. 19, 1988

[54] NOVEL PHOSPHORUS COMPOUNDS FOR PROTECTING CULTIVATED PLANTS FROM THE PHYTOTOXIC ACTION OF HERBICIDES

[75] Inventors: Peter J. Diel, Riehen; Ludwig Maier, Arlesheim, both of Switzerland

[73] Assignee: Ciba-Geigy Corporation, Ardsley, N.Y.

[21] Appl. No.: 843,542

[22] Filed: Mar. 25, 1986

Related U.S. Application Data

[63] Continuation-in-part of Ser. No. 669,412, Nov. 8, 1984.

[30] Foreign Application Priority Data

Nov. 15, 1983 [CH] Switzerland ............. 6135/83
Jun. 6, 1984 [CH] Switzerland ............. 2748/84

[51] Int. Cl.$^4$ ............ C07C 125/065; C07F 9/02; C07F 9/28
[52] U.S. Cl. ............ 558/154; 560/159; 564/15; 260/502.4 R; 71/86; 71/87; 71/88; 71/90; 71/92; 71/93; 71/94; 71/98; 71/77; 71/100; 71/103; 71/105; 71/107; 71/108; 71/115; 71/118; 71/120; 71/121; 71/124; 47/57.6
[58] Field of Search ............ 71/77, 86, 118, 87; 558/154, 170; 47/57.6; 560/159; 564/15

[56] References Cited

U.S. PATENT DOCUMENTS

| | | | |
|---|---|---|---|
| 3,133,810 | 5/1964 | Hamm | 71/101 |
| 3,733,192 | 5/1973 | Harris et al. | 71/77 |
| 4,021,224 | 5/1977 | Pallos et al. | 71/77 |
| 4,029,679 | 6/1977 | Koetsch et al. | 558/170 |

FOREIGN PATENT DOCUMENTS 1335846 10/1973 United Kingdom ............ 558/154

OTHER PUBLICATIONS

Advances in Agronomy, vol. 36, Hatzios, p. 265
Chem. Abstracts, 88, 152724n, 1978.
Chem. Abstracts, 95, 204054s, 1981.
Weed Control Handbook, Fryer et al., eds., 5th ed., British Crop Protection Council (1967).
Merck Index, Ninth ed., Windholz et al., eds, Merck and Co. (1976).

*Primary Examiner*—Glennon H. Hollrah
*Assistant Examiner*—Patricia L. Morris
*Attorney, Agent, or Firm*—Edward McC. Roberts

[57] ABSTRACT

Novel acylated hydrazinomethylphosphonic acids, hydrazinomethylphosphonates, hydrazinomethylphosphinic acids, hydrazinomethylphosphinates or hydrazinomethylphosphine oxides of formula I below are able as "antidotes" or "safeners" to protect cultivated plants from the phytotoxic action of herbicides. Suitable crops are preferably maize, sorghum, cereals, rice and soybeans and the herbicides employed are in particular chloroacetanilides.

17 Claims, No Drawings

NOVEL PHOSPHORUS COMPOUNDS FOR PROTECTING CULTIVATED PLANTS FROM THE PHYTOTOXIC ACTION OF HERBICIDES

CROSS-REFERENCE TO RELATED APPLICATION

This is a continuation-in-part of our application Ser. No. 669,412, filed Nov. 8, 1984.

The acylated hydrazinomethylphosphonates, hydrazinomethylphosphinates or hydrazinomethylphosphine oxides have the formula I

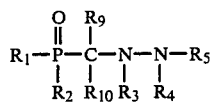

wherein $R_1$ and $R_2$ are each independently hydroxy, alkyl, aryl, phenylalkyl, alkoxy, alkenyloxy, alkynyloxy, aryl or phenylalkoxy, the radicals of which may be substituted, $R_3$ is a halogenated alkanoyl or alkenoyl radical $R_4$ is hydrogen, a halogenated alkanoyl or alkenoyl radical or an alkyl, alkenyl or phenylalkyl radical, or an alkylcarbonyl, alkenylcarbonyl, alkynylcarbonyl or phenylcarbonyl radical which may be unsubstituted or substituted or is an alkoxycarbonyl or phenylalkoxycarbonyl radical which may be unsubstituted or substituted or is an alkoxycarbonyl or phenylalkoxycarbonyl radical which may also be substituted, $R_5$ is hydrogen or an alkyl, alkenyl or alkynyl radical which may also be substituted, $R_9$ is hydrogen, alkyl or phenyl which is unsubstituted or substituted and $R_{10}$ is hydrogen or alkyl.

The present invention relates to novel acylated hydrazinomethylphosphonates, hydrazinomethylphosphinates and hydrazinomethylphosphine oxides which, are herbicide antagonists, are able to protect cultivated plants from the phytotoxic action of herbicides, in particular of chloroacetanilide herbicides, to compositions containing an acylated hydrazinomethylphosphonate, hydrazinomethylphosphinate or hydrazinomethylphosphine oxide, and to compositions which, in addition to containing such an antagonist (also called antidote or safener), already contain the herbicide, and to a method of selectively controlling weeds, which comprises the use of a herbicide and said safener. The invention also relates to the preparation of novel acylated hydrazinomethylphosphonates, hydrazinomethylphosphinates and hydrazinomethylphosphine oxides.

It is known that herbicides belonging to a very wide range of compound classes such as triazines, urea derivatives, carbamates, thiocarbamates, haloacetanilides, halophenoxyacetic acids etc., when employed in an effective concentration, often also damage cultivated plants to a certain extent in addition to the weeds which it is desired to control. Too high concentrations are often applied unintentionally and randomly whenever peripheral zones overlap on zonal spraying, whether as a consequence of the action of wind or through miscalculating the sweep of the spray device employed. The climatic conditions or the nature of the soil may be such that the concentration of herbicide recommended for normal conditions acts as an overdose. The quality of the seeds may also be a factor in the tolerance of the herbicide. To counteract this problem, different compounds have already been proposed which are able specifically to antagonise the harmful action of the herbicide on the cultivated plant, i.e. to protect the cultivated plant without noticeably influencing the herbicidal action on the weeds to be controlled.

However, it has been found that the proposed antidotes very often have a species-specific activity both with respect to the cultivated plants and to the herbicide and also, in some cases, contingent on the mode of application, i.e. a specific antidote is often suitable only for a specific cultivated plant and a few classes of herbicides.

The direct pre- or postemergence treatment of certain useful plants with antidotes as antagonists of specific classes of herbicides in a crop area is disclosed in German Offenlegungsschrift specifications Nos. 2 141 586 and 2 218 097 and in U.S. Pat. No. 3 867 444.

Further, German Offenlegungsschrift No. 2 402 983 discloses that maize plants can be effectively protected against damage by chloroacetanilides by adding an N-disubstituted dichloroacetamide as antidote to the soil.

The compounds of the present invention are able to protect cultivated plants such as cereals, maize, rice, sorghum or soybeans from the phytotoxic action of herbicides belonging to different chemical classes.

The novel acylated hydrazinomethylphosphonic acids, hydrazinomethylphosphonates, hydrazinomethylphosphinic acids, hydrazinomethylphosphinates and hydrazinomethylphosphine oxides have the formula I

wherein $R_1$ and $R_2$ are each independently hydroxy, $C_1$–$C_4$alkyl, aryl, $C_1$–$C_4$alkoxy, $C_2$–$C_4$alkenyloxy, $C_2$–$C_4$alkynyloxy, $C_2$–$C_4$haloalkoxy containing 1 to 5 halogen atoms, $C_2$–$C_8$alkoxyalkoxy, $C_1$–$C_4$cyanoalkoxy, or are $C_1$–$C_4$phenylalkyl or aralkoxy which is unsubstituted or substituted in the phenyl nucleus by halogen, cyano, nitro or $C_1$–$C_4$alkyl, $R_3$ is a haloalkanoyl radical —$COCX_1X_2$—$R_6$ or an alkenoyl radical which is is substituted by 1 to 3 halogen atoms and contains 2 to 4 carbon atoms in the alkenyl moiety, $R_4$ is hydrogen or a substituent as defined for $R_3$, or is a —$COOR_7$ or —$COR_8$ radical or a $C_1$–$C_4$alkyl or $C_2$–$C_4$alkenyl radical, or is a $C_1$–$C_4$phenylalkyl radical which is unsubstituted or substituted in the phenyl ring by halogen, cyano, nitro or $C_1$–$C_4$alkoxy, $R_5$ is hydrogen or a $C_1$–$C_4$alkyl, $C_2$–$C_4$alkenyl or $C_2$–$C_4$alkynyl radical, $R_6$ is hydrogen, halogen or a $C_1$–$C_6$alkyl radical, $R_7$ is a $C_1$–$C_4$alkyl radical or a $C_1$–$C_4$phenylalkyl radical which is unsubstituted or substituted in the phenyl ring by halogen, cyano, nitro or $C_1$–$C_4$alkoxy, $R_8$ is a $C_1$–$C_4$alkyl, $C_2$–$C_4$alkenyl or $C_2$–$C_4$alkynyl radical, or is a phenyl or $C_1$–$C_4$phenylalkyl radical which is unsubstituted or substituted by halogen, cyano, nitro or $C_1$–$C_4$alkoxy, $R_9$ is hydrogen, $C_1$–$C_4$alkyl, or phenyl which is unsubstituted or substituted by halogen, cyano, nitro or $C_1$–$C_4$alkoxy, $R_{10}$ is hydrogen or $C_1$–$C_4$alkyl and $X_1$ and $X_2$ are each halogen or one of $X_1$ and $X_2$ is also hydrogen.

Alkyl by itself or as moiety of another substituent may be methyl, ethyl, n-propyl and isopropyl, and n-butyl, isobutyl, sec-butyl and tert-butyl. Examples of alkenyl radicals are vinyl, allyl, methallyl, butenyl and butadienyl. Examples of alkynyl radicals are ethynyl, propynyl and butynyl.

Aralkyl radicals comprise phenyl and naphthyl radicals which are linked through $C_1$–$C_4$alkyl. Aralkyl is preferably phenylethyl and, most preferably, benzyl.

Halogen is fluorine, chlorine, bromine and iodine, with chlorine being preferred.

Effective safeners are such compounds of formula I, wherein $R_1$ and $R_2$ are each $C_1$–$C_4$alkoxy (phosphonates), $R_1$ is $C_1$–$C_4$alkoxy and $R_2$ is $C_1$–$C_4$alkyl (phosphinates), $R_1$ and $R_2$ are each $C_1$–$C_4$alkyl (phosphine oxides), and such compounds, wherein each of $R_1$ and $R_2$ is a $C_1$–$C_4$alkyl or $C_1$–$C_4$alkoxy radical, $R_3$ is the chloroacetyl, dichloroacetyl or 2,3,3-trichloroacrylic acid radical, $R_4$ is hydrogen or a substituent as defined for $R_3$, or is a $C_1$–$C_4$alkyl, $C_2$–$C_4$alkenyl, aralkyl, $C_1$–$C_4$alkylcarbonyl, $C_1$–$C_4$alkoxycarbonyl, benzoyl or benzyloxycarbonyl radical and $R_5$ is hydrogen; and the following compounds:

hydrazino-N-benzyloxycarbonyl-N'-chloroacetyl-N'-methyl-O,O-diethylphosphonate, hydrazino-N-benzyloxycarbonyl-N'-dichloroacetyl-N'-methyl-O,O-diethylphosphonate, hydrazino-N-benzyloxycarbonyl-N'-dichloroacetyl-N'-methyl-O,O-di-isopropyl-phosphonate, hydrazino-N-methoxycarbonyl-N'-chloroacetyl-N'-methyl-O,O-diethylphosphonate, hydrazino-N-methoxycarbonyl-N'-dichloroacetyl-N'-methyl-O,O-diethylphosphonate, hydrazino-N-t-butyloxycarbonyl-N'-chloroacetyl-N'-methyl-O,O-diethylphosphonate, hydrazino-N-t-butyloxycarbonyl-N'-dichloroacetyl-N'-methyl-O,O-diethylphosphonate, hydrazino-N'-chloroacetyl-N'-methyl-O,O-diethylphosphonate, hydrazino-N-benzyloxycarbonyl-N'-dichloroacetyl-N'-methyl-O-isopropyl-methylphosphinate, hydrazino-N-benzyloxycarbonyl-N'-dichloroacetyl-N'-methyl-O-ethyl-methylphosphinate and hydrazino-N-benzyloxycarbonyl-N'-dichloroacetyl-N'-methyl-O-ethyl-ethylphosphinate.

The preparation of the novel acylated hydrazinomethylphosphonates, hydrazinomethylphosphinates and hydrazinomethylphosphine oxides of formula I is effected in a manner known per se.

The synthesis steps may be illustrated for example by the following equations:

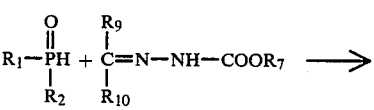

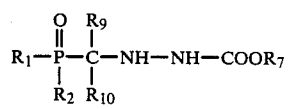

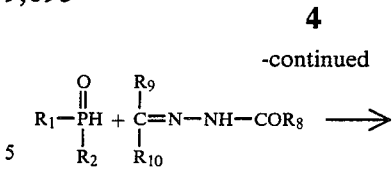

The derivative of the respective phosphorous, phosphonic or phosphinic acid is condensed with an alkylidenehydrazine which is protected by a carbonic acid radical thus affording an acylated hydrazinomethylphosphonate, hydrazinomethylphosphinate or hydrazinomethylphosphine oxide.

If $R_1$ and $R_2$ are alkyl radicals, an acylated hydrazinomethylphosphine oxide is also obtained as follows:

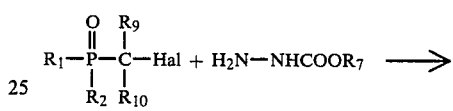

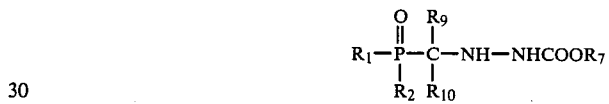

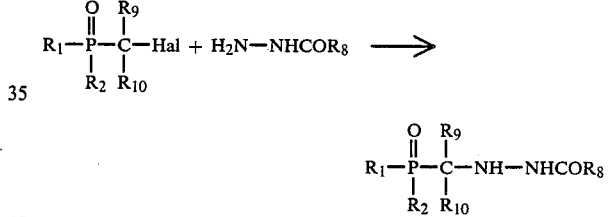

The halomethylphosphine oxide is condensed with a carbazate.

These condensation reactions are carried out in an inert organic solvent.

The protective group —COOR$_7$ can, if desired, be removed

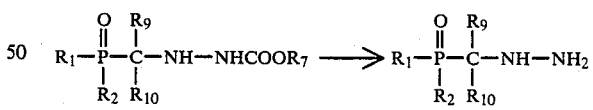

This removal is effected by simple hydrolysis in alkaline or acidic medium or also by hydrogenolysis in acidic medium with hydrogen and a catalyst such as palladium on activated carbon if $R_7$ is benzyl.

The above mentioned hydrazinomethylphosphonyl, hydrazinomethylphosphinyl and hydrazinomethyloxophosphino derivatives can be acylated with 1 or 2 molar equivalents of haloalkanoyl halide or haloalkenoyl halide.

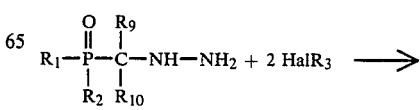

-continued

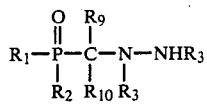

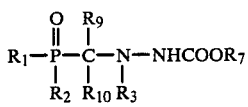

These reactions are carried out at low temperature in the range from −20° C. to +50° C. in an inert organic solvent in the presence of at least an equimolar amount of an acid acceptor.

If $R_4$ or $R_5$ is an alkyl, alkenyl, alkynyl or aralkyl radical, said radicals may be introduced into a compound of formula I by alkylating an acylated hydrazinomethylphosphonate, hydrazinomethylphosphinate or hydrazinomethylphosphine oxide of the formula below with X—$R_8$

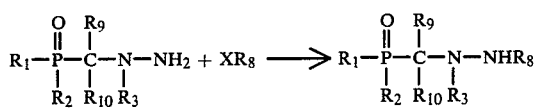

These reactions are carried out in an inert organic solvent in the presence of at least an equimolar amount of an acid acceptor.

In the above equations $R_1$, $R_2$, $R_3$, $R_5$, $R_7$, $R_9$ and $R_{10}$ are as defined for formula I, Hal is halogen, preferably chlorine or bromine. The process of the present invention for the preparation of a compound of formula I comprises a hydrazinomethylphosphonate, hydrazinomethylphosphinate or hydrazinomethylphosphine oxide of formula II

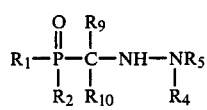     (II)

wherein
$R_1$, $R_2$, $R_4$, $R_5$, $R_9$ and $R_{10}$ are as defined for formula I, in an inert organic solvent in the presence of at least an equimolar equivalent of an acid acceptor with an acyl halide of formula III

    (III), wherein
$R_3$ is as defined for formula I and Hal is chlorine or bromine.

Suitable inert organic solvents for these reactions are in particular halogenated hydrocarbons such as chloroform, methylene chloride, ethylene chloride and also aromatic compounds such as benzene, toluene or xylene. Further suitable inert organic solvents are ethers such as diethyl ether, dioxane or tetrahydrofuran, higher boiling hydrocarbons such as cyclohexane or dimethylformamide, as well as mixtures of such solvents.

The reaction is carried out in the temperature range from −20° to the boiling point of the solvent. When the condensation reactions exotherm, it is convenient to cool the reaction mixture initially, so long as hydrogen halide envolves, and, at the conclusion of the reactions, after all has been added, to stir the mixture further with heating.

Depending on the end use, the safener or antidote of the formula I can be used for pretreating seeds of the cultivated plant (dressing of the seeds or cuttings) or it can be added to the soil before or after sowing. However, it can also be applied pre- or postemergence by itself alone or together with the herbicide. The treatment of the plant or seeds with the safener can therefore in principle be carried out irrespective of the time of application of the phytotoxic chemical. It can, however, also be carried out by simultaneous application of phytotoxic chemical and safener (tank mixture). The pre-emergence treatment includes both treatment of the crop area before sowing (ppi=pre-plant incorporation) and treatment of the crop areas after sowing but before emergence of the plants.

The rates of application of the safener with respect to the herbicide depend largely on the mode of application. Where a field treatment is carried out, either simultaneously as tank mixture or with separate application of herbicide and safener, the ratio of safener to herbicide is in the range from 1:100 to 5:1. Full protective action is usually obtained at a ratio of safener to herbicide of 1:5 to 1:50. When dressing seeds and taking similar specific protective measures, however, much lower amounts of safener are required compared with e.g. the amounts of herbicide later employed per hectare of crop area. For seed dressing, 0.1 to 10 g of safener per kg of seeds are normally required. Full protection is usually obtained with 0.1 to 2 g of safener per kg of seeds. If it is desired to apply the safener shortly before sowing by seed soaking, antidote solutions which contain the active ingredient in a concentration of 1 to 10'000 ppm are used. For protective action will normally be obtained with safener concentrations of 100 to 1000 ppm.

As a rule there is a substantial interval of time between protective measures such as seed dressing and treatment of seedlings with a safener of the formula I and the possible later field treatment with agricultural chemicals. Pretreated seeds and plants can later come in contact with different chemicals in agriculture, horticulture and forestry. Accordingly, the invention relates to plant protection compositions which contain a safener of the formula I as active ingredient, together with conventional carriers. If appropriate, such compositions may be additionally mixed with the chemical from whose effects it is desired to protect the cultivated plant.

Cultivated plants within the scope of this invention are all plants which, in any form, can be harvested (seeds, roots, stalks, tubers, leaves, blossoms) and from which extracts can be obtained (oils, sugar, starch, protein) and which are cultivated for this purpose. These plants comprise e.g. all species of cereals such as wheat, rye, barley, oats and, in particular, rice, sorghum, maize, and also cotton, sugar beet, sugar cane, soybeans, beans, and peas.

The safener can be employed wherever it is desired to protect a cultivated plant of the kind indicated above from the harmful effects of an agricultural chemical. As already mentioned, possible agricultural chemicals are primarily herbicides of the most widely varying compound classes, in particular haloacetanilides and thiocarbamates.

Numerous haloacetanilides whose harmful effects on cultivated plants can be antagonised with the novel hydrazinomethylphosphonates, hydrazinomethylphosphinates and hydrazinomethylphosphine oxides of the formula I are known in the art (q.v. German patent applications Nos. 2 305 495, 2 328 340, 2 212 268, 2 726 252 and 2 805 757, and U.S. Pat. Nos. 3,946,944, 4,022,608 and 4,039,314). Such haloacetanilides may be illustrated by the general formula VII

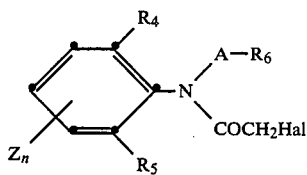

wherein Hal is halogen, preferably chlorine or bromine, each of $R_4$ and $R_5$ independently of the other is hydrogen, halogen, lower alkyl, alkoxy, alkylthio, haloalkyl, alkoxyalkyl or alkylthioalkyl, Z is hydrogen, halogen, lower alkyl, alkoxy, alkylthio, haloalkyl, alkoxyalkyl or alkylthioalkyl, which radicals Z are preferably in the 3-position with respect to the nitrogen atom, n is 0 to 3, A is alkylene, preferably methylene, 1,1-ethylene, and 1,2-ethylene which may be substituted by 1 or 2 lower alkyl groups, and $R_6$ is lower alkoxy, hydroxycarbonyl, alkoxycarbonyl, carbamoyl, N-alkylcarbamoyl, N,N-dialkylcarbamoyl, cyano, an unsubstituted or substituted nitrogen-containing heterocyclic radical, alkanoyl, unsubstituted or substituted benzoyl, unsubstituted or substituted 1,3,4-oxadiazol-2-yl, 1,3,4-thiadiazol-2-yl, 1,3,4-triazol-3-yl or 1,3,4-triazol-1-yl.

Typical examples of such haloacetanilides are:
N-ethoxymethyl-N-chloroacetyl-2-ethyl-6-methylaniline
N-chloroacetyl-N-methoxymethyl-2,6-diethylaniline
N-chloroacetyl-N-(2-methoxyethyl)-2,6-dimethylaniline
N-(2-allyloxyethyl)-N-chloroacetyl-2,6-dimethylaniline
N-chloroacetyl-N-(2-n-propoxyethyl)-2,6-dimethylaniline
N-chloroacetyl-N-(2-isopropoxyethyl)-2,6-dimethylaniline
N-chloroacetyl-N-(2-methoxyethyl)-2-ethyl-6-methylaniline
N-chloroacetyl-N-(methoxyethyl)-2,6-diethylaniline
N-(2-ethoxyethyl)-N-chloroacetyl-2-ethyl-6-methylaniline
N-chloroacetyl-N-(2-methoxy-1-methylethyl)-2-methylaniline
N-chloroacetyl-N-(2-methoxy-1-methylethyl)-2,6-dimethylaniline
N-chloroacetyl-N-(2-methoxy-1-methylethyl)-2,6-diethylaniline
N-chloroacetyl-N-(2-methoxy-1-methylethyl)-2-ethyl-6-methylaniline
N-(2-ethoxyethyl)-N-chloroacetyl-2,6-diethylaniline
N-chloroacetyl-N-(2-n-propoxyethyl)-2-ethyl-6-methylaniline
N-chloroacetyl-N-(2-n-propoxyethyl)-2,6-diethylaniline
N-chloroacetyl-N-(2-isopropoxyethyl)-2-ethyl-6-methylaniline
N-ethoxycarbonylmethyl-N-chloroacetyl-2,6-dimethylaniline
N-ethoxycarbonylmethyl-N-chloroacetyl-2,6-diethylaniline
N-chloroacetyl-N-methoxycarbonylmethyl-2,6-dimethylaniline
N-chloroacetyl-N-(2,2-diethoxyethyl)-2,6-dimethylaniline
N-chloroacetyl-N-(2-methoxy-1-methylethyl)-2,3-dimethylaniline
N-(2-ethoxyethyl)-N-chloroacetyl-2-methylaniline
N-chloroacetyl-N-(2-methoxyethyl)-2-methylaniline
N-chloroacetyl-N-(2-methoxy-2-methylethyl)-2,6-dimethylaniline
N-(2-ethoxy-2-methylethyl)-N-chloroacetyl-2-ethyl-6-methylaniline
N-chloroacetyl-N-(1-ethyl-2-methoxyethyl)-2,6-dimethylaniline
N-chloroacetyl-N-(2-methoxyethyl)-2-methoxy-6-methylaniline
N-n-butoxymethyl-N-chloroacetyl-2-tert-butylaniline
N-(2-ethoxyethyl-1-methylethyl)-2,6-dimethylaniline
N-chloroacetyl-N-(2-methoxyethyl)-2-chloro-6-methylaniline
N-(2-ethoxyethyl)-N-chloroacetyl-2-chloro-6-methylaniline
N-(2-ethoxyethyl)-N-chloroacetyl-2,3,6-trimethylaniline
N-chloroacetyl-1-(2-methoxyethyl)-2,3,6-trimethylaniline
N-chloroacetyl-N-cyanomethyl-2,6-dimethylaniline
N-but-3-yn-1-yl-N-chloroacetylaniline
N-chloroacetyl-N-propargyl-2-ethyl-6-methylaniline
N-chloracetyl-N-(1,3-dioxolan-2-ylmethyl)-2,6-dimethylaniline
N-chloroacetyl-N-(1,3-dioxolan-2-ylmethyl)-2-ethyl-6-methylaniline
N-chloroacetyl-N-(1,3-dioxan-2-ylmethyl)-2-ethyl-6-methylaniline
N-chloroacetyl-N-(2-furanylmethyl)-2,6-dimethylaniline
N-chloroacetyl-N-(2-furanylmethyl)-2-ethyl-6-methylaniline
N-chloroacetyl-N-(2-tetrahydrofuranylmethyl)-2,6-dimethylaniline
N-chloroacetyl-N-(N-propargylcarbamoylmethyl)-2,6-dimethylaniline
N-chloroacetyl-N-(N,N-dimethylcarbamoylmethyl)-2,6-dimethylaniline
N-(n-butoxymethyl)-N-chloroacetyl-2,6-diethylaniline
N-(2-n-butoxyethyl)-N-chloroacetyl-2,6-diethylaniline
N-chloroacetyl-N-(2-methoxy-1,2-dimethylethyl)-2,6-dimethylaniline
N-chloroacetyl-N-isopropyl-2,3-dimethylaniline
N-chloroacetyl-N-isopropyl-2-chloroaniline
N-chloroacetyl-N-(1H-pyrazol-1-ylmethyl)-2,6-dimethylaniline
N-chloroacetyl-N-(1H-pyrazol-1-ylmethyl)-2-ethyl-6-methylaniline
N-chloroacetyl-N-(1H-1,2,4-triazol-1-ylmethyl)-2,6-dimethylaniline
N-chloroacetyl-N-(1H-1,2,4-triazol-1-ylmethyl)-2,6-diethylaniline
N-benzoylmethyl-N-chloroacetyl-2,6-dimethylaniline
N-benzoylmethyl-N-chloroacetyl-2-ethyl-6-methylaniline
N-chloroacetyl-N-(5-methyl-1,3,4-oxadiazol-2-yl)-2,6-diethylaniline N-chloroacetyl-N-(5-methyl-1,3,4-oxadiazol-2-yl)-2-ethyl-6-methylaniline
N-chloroacetyl-N-(5-methyl-1,3,4-oxadiazol-2-yl)-2-tert-butylaniline
N-chloroacetyl-N-(4-chlorobenzoylmethyl)-2,6-dimethylaniline
N-chloroacetyl-N-(1-methyl-5-methylthio-1,3,4-triazol-2-ylmethyl)-2,6-diethylaniline.

In addition to chloroacetanilides, other classes of herbicides are also suitable, for example thiocarbamates:
S-ethyl-N,N-dipropylthiocarbamate
S-ethyl-N,N-diisopropylthiocarbamate
S-2,3-dichlorallyl-N,N-diisopropylthiocarbamate
S-propyl-N-butyl-N-ethylthiocarbamate
S-2,3,3-trichloroallyl-N,N-diisopropylthiocarbamate
S-propyl-N,N-dipropylthiocarbamate
S-ethyl-N-ethyl-N-cyclohexylthiocarbamate
S-ethyl-N-hexahydro-1H-azepine-1-carbothioate
S-isopropyl-N,N-hexamethylene-thiocarbamate
S-(p-chlorobenzyl)-N,N-diethylthiocarbamate
N-ethylthiocarbonyl-cis-decahydroquinoline
N-propylthiocarbonyl-decahydroquinaldine
S-ethyl-N,N-bis(n-butyl)-thiocarbamate
S-tert-butyl-N,N-bis(n-propyl)-thiocarbamate.

In addition to the chloroacetanilides and thiocarbamates, other classes of herbicides are also suitable, for example:
Triazines and triazinones: 2,4-bis(aminopropylamino)-6-methylthio-1,3,5-triazine ("prometryn"), 2,4-bis(ethylamino)-6-methylthio-1,3,5-triazine ("symetrin"), 2-(1',2'-dimethylpropylamino)-4-ethylamino-6-methylthio-1,3,5-triazine ("dimethametryn"), 4-amino-6-tert-butyl-4,5-dihydro-3-methylthio-1,2,4-triazin-5-one ("metribuzin"), 2-chloro-4-ethylamino-6-isopropylamino-1,3,5-triazine ("atrazin"), 2-chloro-4,6-bis(ethylamino)-1,3,5-triazine ("simazin"), 2-tert-butylamino-4-chloro-6-ethylamino-1,3,5-triazine ("terbuthylazin"), 2-tert-butylamino-4-ethylamino-6-methoxy-1,3,5-triazine ("terbumeton"), 2-tert-butylamino-4-ethylamino-6-methylthio-1,3,5-triazine ("terbutryn"), 2-ethylamino-4-isopropylamino-6-methylthio-1,3,5-triazine ("ametryn"),
Ureas: 1-(benzothiazol-2-yl)-1,3-dimethylurea; phenylureas such as 3-(3-chloro-p-tolyl)-1,1-dimethylurea ("chlortoluron"), 1,1-dimethyl-3-($\alpha,\alpha,\alpha$-trifluoro-m-tolyl)urea ("fluormeturon"), 3-(4-bromo-3-chlorophenyl)-1-methoxy-1-methylurea ("chlorbromuron"), 3-(4-bromophenyl)-1-methoxy-1-methylurea ("metobromuron"), 3-(3,4-dichlorophenyl)-1-methoxy-1-methylurea ("linuron"), 3-(4-chlorophenyl)-1-methoxy-1-methylurea ("monolinuron"), 3-(3,4-dichlorophenyl)-1,1-dimethylurea ("diuron"), 3-(4-chlorophenyl)-1,1-dimethylurea ("monuron"), 3-(3-chloro-4-methoxyphenyl)-1,1-dimethylurea ("metoxuron"); sulfonylureas, e.g. N-(2-chlorophenylsulfonyl)-N'-(4-methoxy-6-methyl-1,3,5-triazin-2-yl)urea, N-(2-methoxycarbonylphenylsulfonyl)-N'-(4,6-dimethylpyridin-2-yl)urea, N-(2,5-dichlorophenylsulfonyl)-N'-(4,6-dimethoxypyrimidin-2-yl)urea, N-[2-(2-butenyloxy)phenylsulfonyl]-N'-(4-methoxy-6-methyl-1,3,5-triazin-2-yl)urea, as well as the sulfonylureas listed in European patent publications Nos. 44808 and 44809;
Chloroacetamides: N-[1-isopropyl-2-methylpropen-1-yl(1)]-N-(2'-methoxyethyl)-chloroacetamide.
Diphenyl ethers and nitrodiphenyl ethers: 2,4-dichlorophenyl-4'-nitrophenyl ether ("nitrofen"), 2-chloro-1-(3'-ethoxy-4'-nitrophenoxy)-4-trifluoromethylbenzene ("oxyfluorfen"), 2',4'-dichlorophenyl-3-methoxy-4-nitrophenyl ether ("chlormethoxynil"), methyl-2-[4'-(2'',4''-dichlorophenoxy)phenoxy]propionate, N-(2'phenoxyethyl)-2-[5'(2''-chloro-4''[trifluoromethylphenoxy)phenoxy]-propionamide, 2-methoxyethyl-2-[2-nitro-5-(2-chloro-4-trifluoromethylphenoxy)-phenoxy]propionate; 2-chloro-4-trifluoromethylphenyl-3'-oxazolin-2'-yl-4'-nitrophenyl ether;
Benzoic acid derivatives: methyl-5-(2',4'-dichlorophenoxy)-2-nitrobenzoate ("bifenox"), 5-(2-chloro-4'-trifluoromethylphenoxy)-2-nitrobenzoic acid ("acifluorfen"), 2,6-dichlorobenzonitrile ("dichlobenil").
Nitroanilines: 2,6-dinitro-N,N-dipropyl-4-trifluoromethylaniline ("trifluralin"), N-(1'-ethylpropyl)-2,6-dinitro-3,4-xylidine ("pendimethalin").
Oxadiazolones: 5-tert-butyl-3-(2',4'-dichloro-5'-isopropoxyphenyl)-1,3,4-oxadiazol-2-one ("oxadiazon").
Phosphates: S-2-methylpiperidinocarbonylmethyl-O,O-dipropylphosphorodithioate ("piperophos").
Pyrazoles: 1,3-dimethyl-4-(2',4'-dichlorobenzoyl)-5-(4'-tolylsolfonyloxy)pyrazole.

Other suitable herbicides are α-(phenoxyphenoxy)propionic acid derivatives and α-(pyridyl-2-oxyphenoxy)propionic acid derivatives.

The concentration of safener, provided it is not used for seed dressing, varies from about 0.01 to 5 parts by weight per part by weight of herbicide. The most suitable ratio for achieving optimum effects in the particular cultivated plant is determined from case to case, i.e. depending on the type of herbicide employed.

The compounds of formula I are used in unmodified form or, preferably, as compositions, together with the adjuvants conventionally employed in formulation technology, and are therefore formulated in known manner to emulsifiable concentrates, directly sprayable or dilutable solutions, dilute emulsions, wettable powders, soluble powders, dusts, granulates, and also encapsulations in e.g. polymeric substances. As with the nature of the compositions, the methods of application such as spraying, atomising, dusting, scattering or pouring are chosen in accordance with the intended objectives and the prevailing circumstances.

The formulations, i.e. the compositions containing the compound of the formula I and, where appropriate, a solid or liquid adjuvant, are prepared in known manner, e.g. by homogeneously mixing and/or grinding the active ingredients with extenders, e.g. solvents, solid carriers and, where appropriate, surface-active compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol, ethylene glycol monomethyl or monoethyl ether, ketones such as cyclohexanone, strongly polar solvents such as N-methyl-2-pyrrolidone, dimethylsulfoxide or dimethylformamide, as well as vegetable oils or epoxidised vegetable oils such as epoxidised coconut oil or soybean oil; or water.

The solid carriers used e.g. for dusts and dispersible powders are normally natural mineral fillers such as calcite, talcum, kaolin, montmorillonite or attapulgite. In order to improve the physical properties it is also possible to add highly dispersed silicic acid or highly dispersed absorbent polymers. Suitable granulated adsortive carriers are porous types, for example pumice, broken brick, sepiolite or bentonite; and suitable non-sorbent carriers are materials such as calcite or sand. In addition, a great number of pregranulated materials of inorganic or organic nature can be used, e.g. especially dolomite or pulversed plant residues.

Depending on the nature of the compound of the formula I to be formulated, suitable surface-active compounds are nonionic, cationic and/or anionic surfactants having good emulsifying, dispersing and wetting properties. The term "surfactants" will also be understood as comprising mixtures of surfactants.

Suitable anionic surfactants can be both water-soluble soaps and water-soluble synthetic surface-active compounds.

Suitable soaps are the alkali metal salts, alkaline earth metal salts or unsubstituted or substituted ammonium salts of higher fatty acids ($C_{10}$–$C_{22}$), e.g. the sodium or potassium salts of oleic or stearic acid, or of natural fatty acid mixtures which can be obtained e.g. from coconut oil or tallow oil. Mention may also be made of fatty acid methyltaurin salts.

More frequently, however, so-called synthetic surfactants are used, especially fatty sulfonates, fatty sulfates, sulfonated benzimidazole derivatives or alkylarylsulfonates.

The fatty sulfonates or sulfates are usually in the form of alkali metal salts, alkaline earth metal salts or unsubstituted or substituted ammonium salts and contain a $C_8$–$C_{22}$alkyl radical which also includes the alkyl moiety of acyl radicals, e.g. the sodium or calcium salt of lignosulfonic acid, of dodecylsulfate or of a mixture of fatty alcohol sulfates obtained from natural fatty acids. These compounds also comprise the salts of sulfuric acid esters and sulfonic acids of fatty alcohol/ethylene oxide adducts. The sulfonated benzimidazole derivatives preperably contain 2 sulfonic acid groups and one fatty acid radical containing 8 to 22 carbon atoms. Examples of alkylarylsulfonates are the sodium, calcium or triethylanolamine salts of dodecylbenzenesulfonic acid, of dibutylnaphthalenesulfonic acid or of a naphthalenesulfonic acid/formaldehyde condensation product. Also suitable are corresponding phosphates, e.g. salts of the phosphoric acid ester of an adduct of p-nonylphenol with 4 to 14 moles of ethylene oxide, or phospholipids.

Non-ionic surfactants are preferably polyglycol ether derivatives of aliphatic or cycloaliphatic alcohols, or saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediamine propylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenolpolyethoxyethanols, castor oil polyglycol ethers, polypropylene/polyethylene oxide adducts, tributylphenoxypolyethoxyethanol, polyethylene glycol and octylphenoxyethoxyethanol. Fatty acid esters of polyoxyethylene sorbitan and polyoxyethylene sorbitan trioleate are also suitable non-ionic surfactants.

Cationic surfactants are preferably quaternary ammonium salts which contain, as N-substituent, at least one $C_8$–$C_{22}$alkyl radical and, as further substituents, lower unsubstituted or halogenated alkyl, benzyl or lower hydroxyalkyl radicals. The salts are preferably in the form of halides, methylsulfates or ethylsulfates, e.g. stearyltrimethylammonium chloride or benzyldi(2-chloroethyl)ethylammonium bromide.

The surfactants customarily employed in the art of formulation are described e.g. in the following publications:

"McCutcheon's Detergents and Emulsifiers Annual", MC Publishing Corp. Ridgewood, N.J., 1981; H. Stache, "Tensid-Taschenbuch", 2nd Edition, C. Hanser Verlag, Munich & Vienna, 1981; M. and J. Ash, "Encyclopedia of Surfactants", Vol. I–III, Chemical Publishing Co., New York, 1980–81.

The herbicidal compositions usually contain 0.1 to 95%, preferably 0.1 to 80%, of a compound of the formula I, 1 to 99.9%, of a solid or liquid adjuvant, and 0 to 25%, preferably 0.1 to 25%, of a surfactant.

Preferred formulations are composed in particular of the following constituents (%=percentage by weight):

| | | |
|---|---|---|
| Emulsifiable concentrates | | |
| active ingredient: | 1 to 20%, | preferably 5 to 10% |
| surfactant: | 5 to 30%, | preferably 10 to 20% |
| liquid carrier: | 50 to 94%, | preferably 70 to 85% |
| Dusts | | |
| active ingredient: | 0.1 to 10%, | preferably 0.1 to 1% |
| solid carrier: | 99.9 to 90%, | preferably 99.9 to 99% |
| Suspension concentrates | | |
| active ingredient: | 5 to 75%, | preferably 10 to 50% |
| water: | 94 to 25%, | preferably 90 to 30% |
| surfactant: | 1 to 40%, | preferably 2 to 30% |
| Wettable powders | | |
| active ingredient: | 0.5 to 90%, | preferably 1 to 80% |
| surfactant: | 0.5 to 20%, | preferably 1 to 15% |
| solid carrier: | 5 to 95%, | preferably 15 to 90% |
| Granulates | | |
| active ingredient: | 0.5 to 30%, | preferably 3 to 15% |
| solid carrier: | 99.5 to 70%, | preferably 97 to 85%. |

Whereas commercial products will be preferably formulated as concentrates, the end user will normally employ dilute formulations. The formulations can be diluted to a concentration as low as 0.001% The rates of application are normally from 0.01 to 10 kg a.i./ha, preferably from 0.025 to 5 kg a.i./ha.

The compositions may also contain further ingredients such as stabilisers, antifoams, viscosity regulators, binders, tackifiers, as well as fertilisers and other compounds for obtaining special effects.

The invention is illustrated by the following Examples in which the temperatures are indicated in degrees Celsius (°C.) and the pressures in millibars (mbar).

EXAMPLE 1

Preparation of hydrazino-N-benzyloxycarbonyl-N'-methyldiethylphosphonate (intermediate)

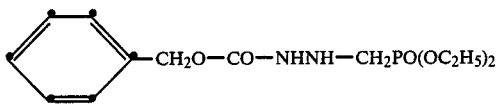

15 g of N-methylenebenzyl carbazate are mixed with 12.2 ml of diethyl phosphite at room temperature and heated with stirring to 110°. 1 ml of boron trifluoride etherate is added and stirring is continued for 1½ hours at 110°–115°, the mixture is cooled and then taken up in methylene chloride at room temperature. The solvent is removed by evaporation and the residue dried under high vacuum affording 23.4 g of an orange-brown oil which crystallises on standing.

Melting point: 56°–57°.

Analysis calculated: C 49.37%, H 6.69%, N 8.86%, P 9.79%, found: C 48.6%, H 6.6%, N 9.0%, P 9.8%.

Instead of boron trifluoride etherate, gaseous hydrochloric acid, tin chloride or an alkali metal alcoholate can be used as catalyst. The reaction can also be carried out without a catalyst but in that case at a higher temperature. Instead of methylene chloride, an aromatic solvent such as benzene, toluene or xylene can be used.

The N-methylenebenzyl carbazate used as starting material was prepared as follows:

A mixture of 102.3 g of benzyl carbazate and 20.3 g of paraformaldehyde in 800 ml of methanol is heated to 50°. 11.06 ml of triethylamine are added and the mixture is stirred for 2 hours under reflux. The solvent is removed by rotary evaporation. The viscous residue is dissolved in methanol, treated with activated carbon and filtered and the filtrate is concentrated. The residue is dried under a vacuum of 1 mbar and at 50° affording 105 g of the title compound as a white powder with a melting point of 87°–91°. According to the NMR spectrum the product is obtained as monomer. It contains 0.03% water of crystallisation.

Analysis calculated: C 60.51%, H 5.68%, N 15.68%, found: C 60.5%, H 5.8%, N 15.6%.

20 g of benzyl carbazate hydrochloride are dissolved in 200 ml of water. 15 ml of a 37% formaline solution are stirred in dropwise at circa 15°. After 2 hours the precipitate is filtered with suction, stirred in two 300 ml portions of water and each time filtered with suction. The precipitate is then dissolved in methylene chloride, the solution is dried over sodium sulfate and filtered. The solvent is distilled off and the residue is dried in vacuo affording 15.9 g of N-methylenebenzyl carbazate which melts at 125°–127°. According to the NMR spectrum the product is obtained as trimer.

Analysis calculated: C 60.67%, H 5.66%, N 15.72%, found: C 60.2%, H 5.5%, N 15.8%.

N-methylenecarbazoyl methylester ($CH_2$=N—NH—$COOCH_3$),

N-methylenecarbazoyl ethylester ($CH_2$=N—NH—$COOC_2H_5$) and

N-methylenecarbazoyl t-butylester ($CH_2$=N—NH—COO t-$C_4H_9$) can be obtained

N=methylenecarbazoyl-β-trichloromethylester ($CH_2$=N—NH—$COOCH_2CCl_3$)

N-methylenecarbazoyl-α,α-dimethyl-β-trichloroethylester ($CH_2$=N—NHCOOC($CH_3$)$_2Cl_3$)

N-methylenecarbazoyl-4-nitrobenzylester

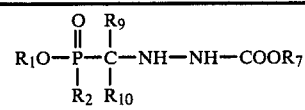

in similar manner.

The following N-phosphomethylhydrazino compounds can be obtained in the manner described in Example 1:

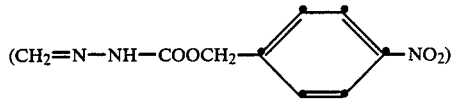

| $R_1$ | $R_2$ | $R_7$ | $R_9$ | $R_{10}$ | Physical data |
|---|---|---|---|---|---|
| $iC_3H_7$ | $iC_3H_7O$ | benzyl | H | H | b.p. 195°/1.1 mbar<br>Analysis |
| $C_2H_5$ | $CH_3$ | benzyl | H | H | cal. C 49.0% H 6.8% N 9.5% P 10.5%<br>found C 49.2% H 6.8% N 9.5% P 10.3% |
| $C_2H_5$ | $C_2H_5$ | benzyl | H | H | cal. C 52.0% H 7.05% N 9.33% P 10.32%<br>found C 51.5% H 7.1% N 9.3% P 10.1% |
| $iC_3H_7$ | $CH_3$ | benzyl | H | H | cal. C 52.0% H 7.05% N 9.33% P 10.32%<br>found C 51.1% H 7.0% N 9.3% P 10.0% |
| $iC_4H_9$ | $CH_3$ | benzyl | H | H | m.p. 58–60° |
| $iC_3H_7$ | $C_3H_7O$ | $CH_3$ | H | H | b.p. 138–140°/0.2 mbar |
| $C_2H_5$ | $C_2H_5O$ | $CH_3$ | H | H | b.p. 160–165°/0.2 mbar |
| $iC_4H_9$ | $CH_3$ | $CH_3$ | H | H | b.p. 170–173°/0.2 mbar |
| $iC_4H_9$ | $CH_3$ | $C_2H_5$ | H | H | b.p. 173–175°/0.2 mbar |
| $iC_3H_7$ | $iC_3H_7O$ | $C_2H_5$ | H | H | b.p. 160°/0.06 mbar |
| $C_2H_5$ | $C_2H_5O$ | $C_2H_5$ | H | H | b.p. 170°/0.1 mbar<br>Analysis |
| $C_2H_5$ | $C_2H_5O$ | t-$C_4H_9$ | H | H | cal. C 42.55% H 8.21% N 9.93% P 10.98%<br>found C 42.9% H 8.6% N 10.4% P 10.6% |
| $iC_4H_9$ | $CH_3$ | t-$C_4H_9$ | H | H | m.p. 75–77°<br>Analysis |
| $C_2H_5$ | $C_2H_5O$ | $C_2H_5$ | H | $C_2H_5$ | cal. C 42.55% H 8.2% N 9.93% P 10.9%<br>found C 42.9% H 7.9% N 9.93% P 10.1% |
| $C_2H_5$ | $C_2H_5O$ | $C_2H_5$ | $CH_3$ | $CH_3$ | cal. C 42.55% H 7.9% N 9.93% P 10.9%<br>found C 42.3% H 8.% N 9.93% P 10.4% |

-continued

| | | | | | |
|---|---|---|---|---|---|
| $C_2H_5$ | $C_2H_5O$ | $C_2H_5$ | H | $C_6H_5$ | oil |
| $C_2H_5$ | $CH_3$ | $C_2H_5$ | $CH_3$ | $CH_3$ | cal. C 42.8% H 8.4% N 11.1% P 12.2% |
| | | | | | found C 41.8% H 8.2% N 10.9% P 11.8% |
| $C_2H_5$ | $C_2H_5$ | $C_2H_5$ | H | $C_2H_5$ | oil |
| $C_2H_5$ | $C_2H_5$ | $C_2H_5$ | H | $C_6H_5$ | oil |
| $C_2H_5$ | $C_2H_5O$ | $CH_2CCl_3$ | H | H | $N_D^{20}$ 1.4792 |
| $C_2H_5$ | $C_2H_5O$ | $C(CH_3)_2CCl_3$ | H | H | m.p. 73–75° |
| $C_2H_5$ | $C_2H_5O$ | p-$NO_2$—benzyl | H | H | $N_D^{20}$ 1.5233 |

$$R_1OP(=O)(R_2)-C(R_9)(R_{10})-NH-NH-COR_8$$

| $R_1$ | $R_2$ | $R_8$ | $R_9$ | $R_{10}$ | Physical data |
|---|---|---|---|---|---|
| | | | | | Analysis |
| $C_2H_5$ | $C_2H_5O$ | Benzyl | H | H | cal. C 52.0% H 7.05% N 9.3% P 10.3% |
| | | | | | found C 51.8% H 7.1% N 9.0% P 10.1% |
| iso$C_3H_7$ | iso$C_3H_7$ | Benzyl | H | H | oil |
| $C_2H_5$ | $CH_3$ | Benzyl | H | H | oil |
| | | | | | Analysis |
| $C_2H_5$ | $C_2H_5O$ | Phenylethyl | H | H | cal. C 53.5% H 7.4% N 8.9% P 9.8% |
| | | | | | found C 53.3% H 7.5% N 8.9% P 9.6% |
| iso$C_3H_7$ | iso$C_3H_7O$ | Phenylethyl | H | H | |
| $C_2H_5$ | $CH_3$ | Phenylethyl | H | H | |

EXAMPLE 2

Preparation of hydrazino-N-ethoxycarbonyl-N'-methylphosphonic acid (intermediate)

$$(HO)_2PO-CH_2-NHNH-COOC_2H_5$$

A sulfurating flask is charged with a solution of 10 g of hydrazino-N-carbethoxy-N-methyl-diisopropylphosphonate in 60 ml of chloroform; 38.5 g of trimethyl bromosilane are added dropwise to the solution with stirring at room temperature. After the trimethyl bromosilane has been added, the mixture is stirred further for 24 hours at room temperature. The solvent is removed by rotary evaporation and the residue is dried under a high vacuum. The semisolid substance is taken up in 20 ml of ethanol, and propylene oxide is added to the solution. After the addition of 60 ml of ether stirring is continued for an hour affording the title compound in the form of white crystals which are filtered off and dried.

Yield: 4.5 g; decomposition point: 204°–206°.

This compound can also be obtained by boiling hydrazino-N-carbethoxy-N'-methyl-diisopropyl-phosphonate for 3 hours in 48% hydrobromic acid.

EXAMPLE 3

Preparation of hydrazinomethyl-O,O-diethylphosphonate $$H_2N-NH-CH_2-PO(OC_2H_5)_2$$

168 g of hydrazino-N-benzyloxycarbonyl-N'-methyl-O,O-diethylphosphonate are dissolved in 2 l of ethanol and the solution is decarboxylated by hydrogenolysis by adding 1.1 molar equivalents of HCl gas and a small amount of 5% palladium on carbon catalyst. After hydrogen absorption has ceased, the catalyst is removed, the alcohol is distilled off under reduced pressure and the residue is taken up in 500 ml of ethyl acetate and 250 ml of water. The phases are separated and the organic phase is extracted again with water. The aqueous phases are combined and concentrated at 50° and 1 mbar. The residue is dried at 50° and 0.05 mbar affording 104.5 g of hydrazino-N-methyl-O,O-diethyl-phosphonate hydrochloride as a yellow oil.

Analysis: calculated: C 25.2%, H 7.4%, N 11.7%, Cl 16.4%, P 13.0%, found: C 25.5%, H 7.3%, N 11.6%, Cl 16.5%, P 13.0%.

The product contains 1.1 molar equivalents of HCl and 0.8 molar equivalent of water of crystallisation.

53.0 g of this hydrochloride are suspended in 1 of methylene chloride and the suspension is cooled to −5°. Then 31.6 g of 30% aqueous NaOH solution are added dropwise with stirring and good cooling. Subsequently an amount of potassium carbonate necessary to bind all the water is added in portions. The methylene chloride solution is decanted off and the potassium carbonate is digested twice with methylene chloride. The organic phases are combined and dried. The solvent is removed by evaporation affording 38.3 g of the title compound as a pale oil.

Spectral:
data: $^1$H NHR $CH_3$ (t, 6H, )1.2 ppm), P—$CH_2$ (d, 2H, 3.08 ppm) $NHNH_2$ (s, 3H, 3.65 ppm), $OCH_2$ (q, 4H, 4.02 ppm) ($CDCl_3$, 60 MHz).

Hydrazinomethyl-O-isobutyl-methyl-phosphinate and its hydrochloride salt were prepared in a manner similar to that described in this Example.

$$iC_4H_9O-P(=O)(CH_3)-CH_2-NH-NH_2 \cdot HCl$$

Spectral:
data: $^1$H NMR $CH_3$ (d, 6H, 0.95 ppm), P—$CH_3$, $$\diagdown CH-(m, 4H, \diagup$$

1.8 ppm) $OCH_2$, P—$CH_2$ (m, 4H, 3.75 ppm), $NHNH_2$ (s, 4.85 ppm) ($D_2O$, 60 MHz).

EXAMPLE 4

Preparation of hydrazinomethyl-methylphosphinic acid (intermediate)

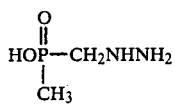

A mixture of 6.8 g of hydrazinomethyl-O-isobutylmethylphosphinate hydrochloride and 50 ml of 6N hydrochloric acid is heated under reflux for 5 hours and subsequently concentrated by rotary evaporation under reduced pressure. The residue is dried under high vacuum at 50° affording 5.6 of a viscous semisolid product which is triturated with ethanol, filtered and dried under high vacuum affording 2.2 g of hydrazinomethylmethylphosphinic acid as a white powder.

$^1$H-NMR (in D$_2$O) CH$_3$P 1.37 (d, J$_{PCH}$ 14 Hz, 3H); CH$_2$P 3.15 (d, J$_{PCH}$ 11 Hz, 2H); NH, OH 4.9 (s) (ppm).

EXAMPLE 5

Preparation of hydrazinomethanephosphonic acid (intermediate)

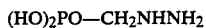

A mixture of 64 g of N-benzoyl-N'-methyl-diethylphosphonylhydrazine and 400 ml of 6N hydrochloric acid is boiled under reflux with stirring for 20 hours while continuously removing alcohol from the reaction mixture by means of a distillation bridge. The reaction mixture is cooled in an ice-bath to 5°, the precipitated benzoic acid is filtered off and washed with a small amount of ice-water. The filtrate and the washings are concentrated by rotary evaporation. The oily residue is dissolved in a small amount of water and adjusted with propylene oxide to pH 4 with stirring and cooling. The resultant precipitate is filtered with suction, washed with a small amount of ice-water and recrystallised from water by adding a small amount of activated carbon affording 12 g (42.6% of theory) of hydrazinomethanephosphonic acid as white ctystals which have a decomposition point of 196°.

EXAMPLE 6

Preparation of hydrazino-N'-chloroacetyl-N'-methyl-O,O-diethylphosphonate

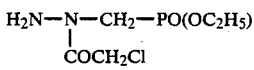

A solution of 20 g of hydrazino-N-benzyloxycarbonyl-N'-chloroacetyl-N'-methyl-O,O-diethylphosphonate in 200 ml of ethanol is hydrogenated by adding 1.1 molar equivalents of HCL gas and a small amount of 5% palladium on carbon catalyst. After oxygen adsorption has ceased, the catalyst is removed and the filtrate is concentrated. The residual oil is taken up in ethyl acetate and water and the phases are separated. The aqueous phase is neutralised with triethylamine and extracted with ether. The combined ethyl acetate and ether phases and dried and concentrated and the residual oil is chromatographed through silica gel eluted with a methylene chloride/methanol (95:5) solution. The solvent is removed by evaporation affording a wax-like product as residue.

Analysis: calculated: C 32.51%, H 6.25%, N 10.83%, Cl 13.71%, P 11.97%, found: C 32.14%, H 6.13%, N 10.77%, Cl 13.48%, P 11.89%.

EXAMPLE 7

Preparation of N,N'-bis-dichloroacetylhydrazinomethyl-O,O-diethylphosphonate

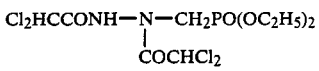

7.0 g (0.0384 mole) of hydrazinomethanephosphonic acid diethylester and 15.3 ml (0.0845 mole) of diisopropylamine are dissolved at −5° in a sulfurating flask in a mixture of 90 ml of tetrahydrofuran and 60 ml of cyclohexane. 8.35 ml (0.0845 mole) of dichloroacetyl chloride are added dropwise to the mixture with cooling and stirring. The mixture is stirred at room temperature for one hour, the amine hydrochloride is filtered with suction and the solvent is removed under a water jet vacuum. The residual brown oil (24.3 g) is dissolved in 250 ml of ethyl acetate. The solution is washed with two 50 ml portions of water, dried and concentrated by rotary evaporation. The residue is dried under high vacuum affording 16.3 g of beige powder. The powder is chromatographed through a column of silica gel eluted with methylene chloride/methanol (95:5). The solvent is removed by evaporation affording 8.1 g of N,N'-dichloroacetlyhydrazinomethanephosphonic acid diethylether with a melting point of 121°–123°.

Analysis: calculated: C 26.76%, H 3.74%, N 6.94%, Cl 35.1%, P 7.67%, found: C 27.0%, H 3.6%, N 6.9%, Cl 34.8%, P 7.7%.

EXAMPLE 8

Preparation of hydrazino-N-benzoylcarbonyl-N'-dichloroacetyl-N'-methyl-O,O-diethylphosphonate.

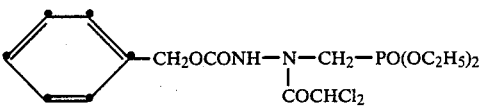

15 g of Hydrazino-N-benzoyloxy-N-methyl-O,O-diethylphosphonate (Example 1) are dissolved in a mixture of 9 ml ethyl-diisopropylamine, 90 ml of tetrahydrofuran and 60 ml of cyclohexane. To this solution is added while stirring at 0° a mixture of 5.1 ml of dichloroacetylchloride in 20 ml cyclohexane tetrahydrofuran 1:1 After everything is added, the reaction mixture is stirred at room-temperature for 3 hours. The ammonium-chloride which has precipitated is then filtered off and the filtrate is evaporated in a rotatory evaporator. The remaining brown oils is purified by chromatography over a silica-gel column with methylenechloride/methanol 95:5- After removal of the solvent, there remains 8.2 g of title product with a wax-like consistency.

Analysis: calculated: C 42.17%, H 4.96%, N 6.65%, Cl 16.6%, P 7.25%, found: C 42.3%, H 4.8%, N 6.6%, Cl 16.7%, P 7.2%.

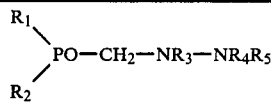

$$\begin{array}{c}R_1\\ \diagdown\\ PO-CH_2-NR_3-NR_4R_5\\ \diagup\\ R_2\end{array}$$

| No. | $R_1$ | $R_2$ | $R_3$ | $R_4$ | $R_5$ | Physical data |
|---|---|---|---|---|---|---|
| 1 | $C_2H_5O$ | $C_2H_5O$ | $COCH_2Cl$ | $COOCH_2C_6H_5$ | H | wax |
| 2 | $C_2H_5O$ | $C_2H_5O$ | $COCHCl_2$ | $COOCH_2C_6H_5$ | H | wax |
| 3 | $iC_3H_7O$ | $iC_3H_7O$ | $COCH_2Cl$ | $COOCH_2C_6H_5$ | H | |
| 4 | $iC_3H_7O$ | $iC_3H_7O$ | $COCHCl_2$ | $COOCH_2C_6H_5$ | H | oil (yellow) |
| 5 | $C_2H_5O$ | $C_2H_5O$ | $COCH_2Cl$ | $COCH_2Cl$ | H | m.p. 98–101° |
| 6 | $iC_3H_7O$ | $iC_3H_7O$ | $COCCl_3$ | $COOC_2H_5$ | H | m.p. 75–77° |
| 7 | $C_2H_5O$ | $C_2H_5$ | $COCH_2Cl$ | $COOCH_2C_6H_5$ | H | |
| 8 | $C_2H_5O$ | $C_2H_5$ | $COCHCl_2$ | $COOCH_2C_6H_5$ | H | m.p. 86–89 |
| 9 | $CH_3$ | $CH_3$ | $COCH_2Cl$ | $COOCH_2C_6H_5$ | H | |
| 10 | $CH_3$ | $CH_3$ | $COCHCl_2$ | $COOCH_2C_6H_5$ | H | |
| 11 | $iC_3H_7O$ | $CH_3$ | $COCHCl_2$ | $COOCH_2C_6H_5$ | H | 87–88° |
| 12 | $C_2H_5O$ | $C_2H_5O$ | $COCH_2Cl$ | $COOCH_3$ | H | oil (yellow) |
| 13 | $C_2H_5O$ | $C_2H_5O$ | $COCHCl_2$ | $COOCH_3$ | H | m.p. 95–98° C. |
| 14 | $iC_4H_9O$ | $CH_3$ | $COCH_2Cl$ | $COOCH_3$ | H | oil |
| 15 | $iC_4H_9O$ | $CH_3$ | $COCHCl_2$ | $COOCH_3$ | H | m.p. 83–86° C. |
| 16 | $CH_3$ | $CH_3$ | $COCH_2Cl$ | $COOCH_3$ | H | |
| 17 | $CH_3$ | $CH_3$ | $COCHCl_2$ | $COOCH_3$ | H | |
| 18 | $C_2H_5O$ | $C_2H_5O$ | $COCH_2Cl$ | $COOC(CH_3)_3$ | H | m.p. 74–80° C. |
| 19 | $C_2H_5O$ | $C_2H_5O$ | $COCHCl_2$ | $COOC(CH_3)_3$ | H | m.p. 112–114° C. |
| 20 | $C_2H_5O$ | $C_2H_5O$ | $COCCl=CCl_2$ | $COOC(CH_3)_3$ | H | m.p. 69–73° C. |
| 21 | $iC_4H_9O$ | $CH_3$ | $COCH_2Cl$ | $COOC(CH_3)_3$ | H | m.p. 93–97° C. |
| 22 | $iC_4H_9O$ | $CH_3$ | $COCHCl_2$ | $COOC(CH_3)_3$ | H | m.p. 76–78° C. |
| 23 | $CH_3$ | $CH_3$ | $COCH_2Cl$ | $COOC(CH_3)_3$ | H | |
| 24 | $CH_3$ | $CH_3$ | $COCHCl_2$ | $COOC(CH_3)_3$ | H | |
| 25 | $C_2H_5O$ | $C_2H_5O$ | $COCCl=CCl_2$ | $COOCH_2C_6H_5$ | H | m.p. 50–53° |
| 26 | $iC_3H_7O$ | $iC_3H_7O$ | $COCCl=CCl_2$ | $COOCH_2C_6H_5$ | H | |
| 27 | $iC_4H_9O$ | $CH_3$ | $COCCl=CCl_2$ | $COOCH_2C_6H_5$ | H | m.p. 107–108° |
| 28 | $C_2H_5$ | $C_2H_5$ | $COCCl=CCl_2$ | $COOCH_2C_6H_5$ | H | |
| 29 | $CH_3$ | $CH_3$ | $COCCl=CCl_2$ | $COOCH_2C_6H_5$ | H | |
| 30 | $C_2H_5O$ | $C_2H_5O$ | $COCCl=CCl_2$ | $COOCH_3$ | H | m.p. 79–82° |
| 31 | $iC_4H_9O$ | $CH_3$ | $COCCl=CCl_2$ | $COOCH_3$ | H | m.p. 124–128° |
| 32 | $C_2H_5$ | $C_2H_5$ | $COCCl=CCl_2$ | $COOCH_3$ | H | |
| 33 | $CH_3$ | $CH_3$ | $COCCl=CCl_2$ | $COOCH_3$ | H | |
| 34 | $C_2H_5O$ | $C_2H_5O$ | $COCCl=CCl_2$ | $COOCd(CH_3)_3$ | H | |
| 35 | $iC_4H_9O$ | $CH_3$ | $COCCl=CCl_2$ | $COOC(CH_3)_3$ | H | m.p. 80–83° |
| 36 | $C_2H_5$ | $C_2H_5$ | $COCCl=CCl_2$ | $COOC(CH_3)_3$ | H | |
| 37 | $CH_3$ | $CH_3$ | $COCCl=CCl_2$ | $COOC(CH_3)_3$ | H | |
| 38 | $C_2H_5O$ | $C_2H_5O$ | $COCH_2Cl$ | $COOC_2H_5$ | H | oil |
| 39 | $C_2H_5O$ | $C_2H_5O$ | $COCHCl_2$ | $COOC_2H_5$ | H | oil |
| 40 | $C_2H_5O$ | $C_2H_5O$ | $COCCl=CCl_2$ | $COOC_2H_5$ | H | m.p. 60–62° |
| 41 | $iC_4H_9O$ | $CH_3$ | $COCH_2Cl$ | $COOC_2H_5$ | H | resin |
| 42 | $iC_4H_9O$ | $CH_3$ | $COCHCl_2$ | $COOC_2H_5$ | H | m.p. 76–78° |
| 43 | $iC_4H_9O$ | $CH_3$ | $COCCl=CCl_2$ | $COOC_2H_5$ | H | m.p. 94–96° |
| 44 | $C_2H_5$ | $C_2H_5$ | $COCH_2Cl$ | $COOC_2H_5$ | H | |
| 45 | $C_2H_5$ | $C_2H_5$ | $COCHCl_2$ | $COOC_2H_5$ | H | m.p. 117–119° |
| 46 | $C_2H_5$ | $C_2H_5$ | $COCCl=CCl_2$ | $COOC_2H_5$ | H | |
| 47 | $CH_3$ | $CH_3$ | $COCH_2Cl$ | $COOC_2H_5$ | H | |
| 48 | $CH_3$ | $CH_3$ | $COCHCl_2$ | $COOC_2H_5$ | H | |
| 49 | $CH_3$ | $CH_3$ | $COCCl=CCl_2$ | $COOC_2H_5$ | H | |
| 50 | $C_2H_5O$ | $C_2H_5O$ | $COCH_2Cl$ | H | H | oil (yellow) |
| 51 | $C_2H_5O$ | $C_2H_5O$ | $COCHCl_2$ | H | H | |
| 52 | $C_2H_5O$ | $C_2H_5O$ | $COCCl=CCl_2$ | H | H | |
| 53 | $C_2H_5O$ | $C_2H_5O$ | $COCHCl_2$ | $COCHCl_2$ | H | m.p. 121–123° |
| 54 | $C_2H_5O$ | $C_2H_5O$ | $COCCl=CCl_2$ | $COOCl_3$ | H | |
| 55 | $iC_4H_9O$ | $CH_3$ | $COCH_2Cl$ | H | H | |
| 56 | $iC_4H_9O$ | $CH_3$ | $COCHCl_2$ | H | H | |
| 57 | $iC_4H_9O$ | $CH_3$ | $COCCl=CCl_2$ | H | H | |
| 58 | $iC_4H_9O$ | $CH_3$ | $COCH_2Cl$ | $COCHCl_2$ | H | |
| 59 | $iC_4H_9O$ | $CH_3$ | $COCHCl_2$ | $COCHCl_2$ | H | m.p. 125–129° |
| 60 | $iC_4H_9O$ | $CH_3$ | $COCl=CCl_2$ | $COCHCl_2$ | H | |
| 61 | $C_2H_5$ | $C_2H_5$ | $COCH_2Cl$ | H | H | |
| 62 | $C_2H_5$ | $C_2H_5$ | $COCHCl_2$ | H | H | |
| 63 | $C_2H_5$ | $C_2H_5$ | $COCCl=CCl_2$ | H | H | |
| 64 | $C_2H_5$ | $C_2H_5$ | $COCH_2Cl$ | $COCHCl_2$ | H | |
| 65 | $C_2H_5$ | $C_2H_5$ | $COCHCl_2$ | $COCHCl_2$ | H | |
| 66 | $C_2H_5$ | $C_2H_5$ | $COCCl=CCl_2$ | $COCHCl_2$ | H | |
| 67 | $CH_3$ | $CH_3$ | $COCH_2Cl$ | H | H | |
| 68 | $CH_3$ | $CH_3$ | $COCHCl_2$ | H | H | |
| 69 | $CH_3$ | $CH_3$ | $COCCl=CCl_2$ | H | H | |
| 70 | $CH_3$ | $CH_3$ | $COCH_2Cl$ | $COCCl=CCl_2$ | H | |
| 71 | $CH_3$ | $CH_3$ | $COCH_2Cl$ | $COCHCl_2$ | H | |
| 72 | $CH_3$ | $CH_3$ | $COCHCl_2$ | $COCHCl_2$ | H | |
| 73 | $C_2H_5O$ | $C_2H_5O$ | $COCH_2Cl$ | $CH_2CH=CH_2$ | H | |
| 74 | $C_2H_5O$ | $C_2H_5O$ | $COCHCl_2$ | $CH_2CH=CH_2$ | H | |
| 75 | $C_2H_5O$ | $C_2H_5O$ | $COCH_2Cl$ | $CH_2C_6H_5$ | H | |

-continued

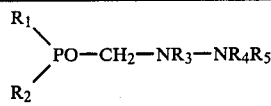

| No. | $R_1$ | $R_2$ | $R_3$ | $R_4$ | $R_5$ | Physical data |
|---|---|---|---|---|---|---|
| 76 | $C_2H_5O$ | $C_2H_5O$ | $COCHCl_2$ | $CH_2C_6H_5$ | H | |
| 77 | $C_2H_5O$ | $C_2H_5O$ | $COCH_2Cl$ | $COCH_3$ | H | |
| 78 | $C_2H_5O$ | $C_2H_5O$ | $COCHCl_2$ | $COCH_3$ | H | |
| 79 | $C_2H_5O$ | $C_2H_5O$ | $COCH_2Cl$ | $COC_6H_5$ | H | |
| 80 | $C_2H_5O$ | $C_2H_5O$ | $COCHCl_2$ | $COC_6H_5$ | H | |
| 81 | $iC_4H_9O$ | $CH_3$ | $COCH_2Cl$ | $C_2H_5$ | H | |
| 82 | $iC_4H_9O$ | $CH_3$ | $COCHCl_2$ | $C_2H_5$ | H | |
| 83 | $iC_4H_9O$ | $CH_3$ | $COCH_2Cl$ | $CH_2C_6H_5$ | H | |
| 84 | $iC_4H_9O$ | $CH_3$ | $COCHCl_2$ | $CH_2C_6H_5$ | H | |
| 85 | $iC_4H_9O$ | $CH_3$ | $COCH_2Cl$ | $COCH_3$ | H | |
| 86 | $iC_4H_9O$ | $CH_3$ | $COCH_2Cl_2$ | $COCH_3$ | H | |
| 87 | $iC_4H_9O$ | $CH_3$ | $COCH_2Cl$ | $COC_6H_5$ | H | |
| 88 | $iC_4H_9O$ | $CH_3$ | $COCHCl_2$ | $COC_6H_5$ | H | |
| 89 | $CH_3$ | $CH_3$ | $COCH_2Cl$ | $C_2H_5$ | H | |
| 90 | $CH_3$ | $CH_3$ | $COCHCl_2$ | $C_2H_5$ | H | |
| 91 | $CH_3$ | $CH_3$ | $COCH_2Cl$ | $CH_2C_6H_5$ | H | |
| 92 | $CH_3$ | $CH_3$ | $COCHCl_2$ | $CH_2C_6H_5$ | H | |
| 93 | $CH_3$ | $CH_3$ | $COCH_2Cl$ | $COCH_3$ | H | |
| 94 | $CH_3$ | $CH_3$ | $COCHCl_2$ | $COCH_3$ | H | |
| 95 | $CH_3$ | $CH_3$ | $COCH_2Cl$ | $COC_6H_5$ | H | |
| 96 | $CH_3$ | $CH_3$ | $COCH_2Cl$ | $COC_6H_5$ | H | |
| 97 | $CH_3$ | $CH_3$ | $COCH_2Cl$ | $CH_2CH=CH_2$ | H | |
| 98 | $CH_3$ | $CH_3$ | $COCHCl_2$ | $CH_2CH=CH_2$ | H | |
| 99 | $iC_3H_7O$ | $iC_3H_7O$ | $COCH_2Cl$ | $COOC_2H_5$ | H | m.p. 64–68° |
| 100 | $iC_3H_7O$ | $iC_3H_7O$ | $COCHCl_2$ | $COOC_2H_5$ | H | m.p. 69–70° |
| 101 | $iC_3H_7O$ | $iC_3H_7O$ | $COCCl=CCl_2$ | $COOC_2H_5$ | H | m.p. 108–110° |
| 102 | $iC_4H_9O$ | $CH_3$ | $COCHCl_2$ | $COOCH_2C_6H_5$ | H | m.p. 84–85° |
| 103 | $iC_4H_9O$ | $CH_3$ | $COCH_2Cl$ | $COOCH_2C_6H_5$ | H | m.p. 82–85° |
| 104 | HO | HO | $COCHCl_2$ | $COOCH_3$ | H | m.p. 145–147°* |
| 105 | HO | HO | $COCHCl_2$ | $COOC_2H_5$ | H | m.p. 92–94°* |
| 106 | $C_2H_5O$ | $CH_3$ | $COCHCl_2$ | $COOCH_2C_6H_5$ | H | oil |
| 107 | $C_2H_5O$ | $CH_3$ | $COCHCl_2$ | $COOCH_3$ | H | m.p. 130–138° |
| 108 | $C_2H_5O$ | $CH_3$ | $COCHCl_2$ | $COOC_2H_5$ | H | m.p. 110–112° |
| 109 | $C_2H_5O$ | $CH_3$ | $COCHCl_2$ | $COOC(CH_3)_3$ | H | m.p. 99–101° |
| 110 | $C_2H_5O$ | $C_2H_5O$ | $COCHCl_2$ | $COOCH_2C_6H_5$ | H | m.p. 106–108° |
| 111 | $C_2H_5O$ | $C_2H_5O$ | $COCHCl_2$ | $COCH_2CH_2C_6H_5$ | H | m.p. 87–89° |
| 112 | $C_2H_5O$ | $CH_3$ | $COCHCL_2$ | $COOCH_2C_6H_5$ | H | m.p. 88–89° |
| 113 | $C_2H_5O$ | $CH_3$ | $COCHCl_2$ | $COCH_2CH_2C_6H_5$ | H | |
| 114 | $iC_3H_7O$ | $iC_3H_7O$ | $COCHCl_2$ | $COOCH_2C_6H_5$ | H | |
| 115 | $iC_3H_7O$ | $iC_3H_7O$ | $COCHCl_2$ | $COCH_2CH_2C_6H_5$ | H | |
| 116 | $iC_3H_7O$ | $iC_3H_7O$ | $COCC_3$ | $COOC_2H_5$ | H | m.p. 75–77° |
| 117 | HO | HO | $COCHCl_2$ | $COOCH_3$ | H | m.p. 145–147°* |
| 118 | HO | HO | $COCHCl_2$ | $COOC_2H_5$ | H | m.p. 92–94°* |

*diisopropylamino salt

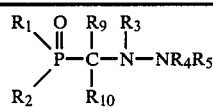

| No. | $R_1$ | $R_2$ | $R_3$ | $R_4$ | $R_5$ | $R_9$ | $R_{10}$ | Physical data |
|---|---|---|---|---|---|---|---|---|
| 119 | $C_2H_5O$ | $C_2H_5O$ | $COCHCl_2$ | $COOC_2H_5$ | H | H | $C_2H_5$ | oil |
| 120 | $C_2H_5O$ | $C_2H_5O$ | $COCHCl_2$ | $COOC_2H_5$ | H | H | Phenyl | m.p. 88–90° |
| 121 | $C_2H_5O$ | $C_2H_5$ | $COCHCl_2$ | $COOC_2H_5$ | H | H | $C_2H_5$ | m.p. 85–88° |
| 122 | $C_2H_5O$ | $C_2H_5$ | $COCHCl_2$ | $COOC_2H_5$ | H | H | Phenyl | |
| 123 | $C_2H_5O$ | $CH_3$ | $COCHCl_2$ | $COOC_2H_5$ | H | $CH_3$ | $CH_3$ | |
| 124 | $C_2H_5O$ | $C_2H_5O$ | $COCHCl_2$ | $COOCH_2CCl_3$ | H | H | H | m.p. 100–107° |
| 125 | $C_2H_5O$ | $C_2H_5$ | $COCHCl_2$ | $COOC(CH_3)_2CCl_3$ | H | H | H | m.p. 111–113° |
| 126 | $C_2H_5O$ | $C_2H_5$ | $COCHCl_2$ | $COOCH_2$<br>$\quad\mid$<br>$C_6H_4(NO_2)_4$ | H | H | H | m.p. 80–82° |

EXAMPLE 8

Formulation Examples for compounds of the formula I or mixtures thereof with herbicides

| (a) Wettable powders | (a) | (b) | (c) |
|---|---|---|---|
| Compound of formula I or mixture thereof with a herbicide | 20% | 60% | 0.5% |
| sodium lignosulfonate | 5% | 5% | 5% |
| sodium laurylsulfate | 3% | — | — |
| sodium diisobutylnaphahalenesulfonate | — | 6% | 6% |
| octylphenol polyethylene glycol ether (7–8 moles of ethylene oxide) | — | 2% | 2% |
| highly dispersed silicic acid | 5% | 27% | 27% |
| kaolin | 67% | — | — |
| sodium chloride | — | — | 59.5% |

The active ingredient is thoroughly mixed with the adjuvants and the mixture is thorougly ground in a suitable mill, affording wettable powders which can be diluted with water to give suspensions of the desired concentration.

| (b) Emulsifiable concentrates | (a) | (b) |
|---|---|---|
| Compound of formula I or mixture thereof with a herbicide | 10% | 1% |
| octylphenol polyethylene glycol ether (4–5 moles of ethylene oxide) | 3% | 3% |
| calcium dodecylbenzenesulfonate | 3% | 3% |
| castor oil polyglycol ether (36 moles of ethylene oxide) | 4% | 4% |
| cyclohexanone | 30% | 10% |
| xylene mixture | 50% | 79% |

Emulsions of any required concentration can be obtained from this concentrate by dilution with water.

| (c) Dusts | (a) | (b) |
|---|---|---|
| Compound of formula I or mixture thereof with a herbicide | 0.1% | 1% |
| talcum | 99.9% | — |
| kaolin | — | 99% |

Dusts which are ready for use are obtained by mixing the active ingredient with the carriers, and grinding the mixture in a suitable mill.

| (d) Extruder granulate | (a) | (b) |
|---|---|---|
| Compound of formula I or mixture thereof with a herbicide | 10% | 1% |
| sodium lignosulfonate | 2% | 2% |
| carboxymethylcellulose | 1% | 1% |
| kaolin | 87% | 96% |

The active ingredient is mixed and ground with the adjuvants, and the mixture is subsequently moistened with water. The mixture is extruded and then dried in a stream of air.

| (e) Coated granulate | |
|---|---|
| Compound of formula or mixture thereof with a herbicide | 3% |
| polyethylene glycol 200 | 3% |
| kaolin | 94% |

The finely ground active ingredient is uniformly applied, in a mixer, to the kaolin moistened with polyethylene glycol. Non-dusty coated granulates are obtained in this manner.

| (f) Suspension concentrate | (a) | (b) |
|---|---|---|
| Compound of formula I or mixture thereof with a herbicide | 40% | 5% |
| ethylene glycol | 10% | 10% |
| nonylphenol polyethylene glycol ether (15 moles of ethylene oxide) | 6% | 1% |
| sodium lignosulfonate | 10% | 5% |
| carboxymethylcellulose | 1% | 1% |
| 37% aqueous formaldehyde solution | 0.2% | 0.2% |
| silicone oil in the form of a 75% aqueous emulsion | 0.8% | 0.8% |
| water | 32% | 77% |

The finely ground active ingredient is intimately mixed with the adjuvants, giving a suspension concentrate from which suspensions of any desired concentration can be obtained by dilution with water.

| (g) Salt solution | |
|---|---|
| Compound of formula I or mixture thereof with a herbicide | 5% |
| isopropylamine | 1% |
| octylphenol polyethylene glycol ether (78 moles of ethylene oxide) | 3% |
| water | 91% |

Biological Examples

The ability of the compounds of formula I to protect cultivated plants from the phytotoxic effects of potent herbicides can be inferred from the following Examples. The compounds of formula I are referred to as safeners in the test procedures.

EXAMPLE 9

Test with herbicide and safener in maize. Preemergence application of herbicide and safener as tank mixture.

Plastic containers measuring 25 cm × 17 cm × 12 cm are filled with sandy loam and LG 5 maize seeds are sown therein. After the seeds have been covered, a dilute solution of the safener to be tested and the herbicide is sprayed as tank mixture onto the surface of the soil. The protective action of the safener is evaluated (in %) 21 days after application. Plants treated with herbicide alone (no protective action) and completely untreated control plants (100% protective action) are used for reference purposes. The results are reported below.

Herbicide: 2-Chloro-2',6'-dimethyl-N-(ethoxymethyl)acetanilide.

Safener: Hydrazino-N-benzyloxycarbonyl-N'-dichloroacetyl-N'-methyl-O,O-diethylphosphonate (Compound 1)

| Herbicide | Safener | Relative protective action in % |
|---|---|---|
| 2 kg/ha | 0.25 kg/ha | 25% |
| 2 kg/ha | 0.125 kg/ha | 25% |
| 4 kg/ha | 0.5 kg/ha | 37.5% |
| 4 kg/ha | 0.25 kg/ha | 25% |
| 6 kg/ha | 0.75 kg/ha | 50% |
| 6 kg/ha | 0.375 kg/ha | 37.5% |

Herbicide: 2-Chloro-2'-ethyl-N-(2''-methoxy-1''-methyl-ethyl)aceto-o-toluidide.

Safener: Hydrazino-N-benzyloxycarbonyl-N'-dichloroacetyl-N'-methyl-O,O-diethylphosphonate (Compound 1)

| Herbicide | Safener | Relative protective action in % |
|---|---|---|
| 2 kg/ha | 0.25 kg/ha | 37.5% |
| 2 kg/ha | 0.125 kg/ha | 37.5% |
| 4 kg/ha | 0.5 kg/ha | 75% |
| 4 kg/ha | 0.25 kg/ha | 75% |
| 6 kg/ha | 0.75 kg/ha | 37.5% |
| 6 kg/ha | 0.375 kg/ha | 37.5% |

Herbicide: 2-Chloro-2',6'-dimethyl-N-(2''-methoxy-1''-methylethyl)acetanilide

| Herbicide Concentration | Safener No. | Safener Concentration | Relative protective action in % |
|---|---|---|---|
| 4 kg/ha | 1 | 2 kg/ha | 63% |
| 4 kg/ha | 1 | 1 kg/ha | 63% |
| 4 kg/ha | 1 | 0.5 kg/ha | 63% |
| 4 kg/ha | 1 | 0.25 kg/ha | 75% |
| 6 kg/ha | 1 | 3 kg/ha | 75% |
| 6 kg/ha | 1 | 1.5 kg/ha | 75% |
| 6 kg/ha | 1 | 0.75 kg/ha | 75% |
| 6 kg/ha | 1 | 0.375 kg/ha | 75% |
| 4 kg/ha | 8 | 2 kg/ha | 50% |
| 4 kg/ha | 8 | 1 kg/ha | 63% |
| 4 kg/ha | 8 | 0.5 kg/ha | 63% |
| 4 kg/ha | 8 | 0.25 kg/ha | 63% |
| 6 kg/ha | 8 | 3 kg/ha | 50% |
| 6 kg/ha | 8 | 1.5 kg/ha | 63% |
| 6 kg/ha | 8 | 0.75 kg/ha | 63% |
| 6 kg/ha | 8 | 0.375 kg/ha | 75% |
| 4 kg/ha | 11 | 2 kg/ha | 38% |
| 4 kg/ha | 11 | 1 kg/ha | 38% |
| 4 kg/ha | 11 | 0.5 kg/ha | 38% |
| 4 kg/ha | 11 | 0.25 kg/ha | 50% |
| 6 kg/ha | 11 | 3 kg/ha | 50% |
| 6 kg/ha | 11 | 1.5 kg/ha | 50% |
| 6 kg/ha | 11 | 0.75 kg/ha | 50% |
| 6 kg/ha | 11 | 0.375 kg/ha | 38% |
| 4 kg/ha | 13 | 2 kg/ha | 50% |
| 4 kg/ha | 13 | 1 kg/ha | 50% |
| 4 kg/ha | 13 | 0.5 kg/ha | 50% |
| 4 kg/ha | 13 | 0.25 kg/ha | 63% |
| 6 kg/ha | 13 | 3 kg/ha | 50% |
| 6 kg/ha | 13 | 1.5 kg/ha | 63% |
| 6 kg/ha | 13 | 0.75 kg/ha | 50% |
| 6 kg/ha | 13 | 0.375 kg/ha | 75% |
| 4 kg/ha | 42 | 2 kg/ha | 63% |
| 4 kg/ha | 42 | 1 kg/ha | 63% |
| 4 kg/ha | 42 | 0.5 kg/ha | 75% |
| 4 kg/ha | 42 | 0.25 kg/ha | 75% |
| 6 kg/ha | 42 | 3 kg/ha | 63% |
| 6 kg/ha | 42 | 1.5 kg/ha | 75% |
| 6 kg/ha | 42 | 0.75 kg/ha | 75% |
| 6 kg/ha | 42 | 0.375 kg/ha | 75% |
| 4 kg/ha | 100 | 2 kg/ha | 50% |
| 4 kg/ha | 100 | 1 kg/ha | 38% |
| 4 kg/ha | 100 | 0.5 kg/ha | 50% |
| 4 kg/ha | 100 | 0.25 kg/ha | 38% |
| 6 kg/ha | 100 | 3 kg/ha | 63% |
| 6 kg/ha | 100 | 1.5 kg/ha | 63% |
| 6 kg/ha | 100 | 0.75 kg/ha | 63% |
| 6 kg/ha | 100 | 0.375 kg/ha | 63% |

What is claimed is:

1. An acylated hydrazinomethylphosphonic acid, hydrazinomethylphosphate, hydrazinomethylphosphinic acid, hydrazinomethylphosphinate or a hydrazinomethylphosphine oxide of the formula

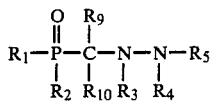

wherein
$R_1$ and $R_2$ are each independently hydroxy, $C_1$–$C_4$alkyl, $C_1$–$C_4$alkoxy,
$R_3$ is a haloalkanoyl radical —$COCX_1X_2$-$R_6$ or an alkenoyl radical which is substituted by 1 to 3 halogen atoms and contains 2 to 4 carbon atoms in the alkenyl moiety,
$R_4$ is hydrogen or a substituent as defined for $R_3$, or is a —$COOR_7$ or —$COR_8$ radical or a $C_1$–$C_4$alkyl or $C_2$–$C_4$-alkenyl radical, or is phenyl-$C_1$–$C_4$alkyl,
$R_5$ is hydrogen or $C_1$–$C_4$alkyl,
$R_6$ is hydrogen or halogen,
$R_7$ is a $C_1$–$C_4$alkyl radical or a $C_1$–$C_4$phenylalkyl radical which is unsubstituted or substituted in the phenyl ring by halogen, cyano, nitro or $C_1$–$C_4$alkoxy,
$R_8$ is $C_1$–$C_4$alkyl, $C_2$–$C_4$alkenyl, $C_2$–$C_4$alkynyl or phenyl,
$R_9$ is hydrogen, $C_1$–$C_4$alkyl, or phenyl,
$R_{10}$ is hydrogen $C_1$–$C_4$alkyl and
$X_1$ and $X_2$ are each halogen or one of $X_1$ and $X_2$ is also hydrogen.

2. An acylated hydrazinomethylphosphonic acid or a hydrazinomethylphosphonate of claim 1, wherein $R_1$ and $R_2$ are each independently hydroxy or $C_1$–$C_4$alkoxy.

3. Hydrazino-N-benzyloxycarbonyl-N'-chloroacetyl-N'-methyl-O,O-diethylphosphonate according to claim 2.

4. Hydrazino-N-benzyloxycarbonyl-N'-dichloroacetyl-N'-methyl-O,O-diethylphosphonate according to claim 2.

5. Hydrazino-N-benzyloxycarbonyl-N'-dichloroacetyl-N'-methyl-O,O-disopropylphosphonate according to claim 2.

6. Hydrazino-N-methoxycarbonyl-N'-chloroacetyl-N'-methyl-O,O-diethylphosphonate according to claim 2.

7. Hydrazino-N-methoxycarbonyl-N'-dichloroacetyl-N'-methyl-O,O-diethylphosphonate according to claim 2.

8. Hydrazino-N-t-butoxycarbonyl-N'-chloroacetyl-N'-methyl-O,O-diethylphosphonate according to claim 2.

9. Hydrazino-N-t-butyloxycarbonyl-N'-dichloroacetyl-N'-methyl-O,O-diethylphosphonate according to claim 2.

10. Hydrazino-N-ethoxycarbonyl-N'-dichloroacetyl-N'-methyl-O,O-diisopropylphosphonate according to claim 2.

11. Hydrazino-N'-chloroacetyl-N'-methyl-O,O-diethylphosphonate according to claim 2.

12. An acylated hydrazinomethylphosphinate of claim 1, wherein $R_1$ is hydroxy or $C_1$–$C_4$alkoxy and $R_2$ is $C_1$–$C_4$alkyl.

13. Hydrazino-N-benzyloxycarbonyl-N'-dichloroacetyl-N'-methyl-O-ethyl-methylphosphinate according to claim 12.

14. Hydrazino-N-benzyloxycarbonyl-N'-dichloroacetyl-N'-methyl-O-isopropyl-methylphosphinate according to claim 12.

15. Hydrazino-N-benzyloxycarbonyl-N'-dichloroacetyl-N'-methyl-O-ethyl-ethylphosphinate according to claim 12.

16. An acylated hydrazinomethylphosphine oxide of claim 1, wherein $R_1$ and $R_2$ are each a $C_1$–$C_4$alkyl radical.

17. An acylated hydrazinomethylphosphonate, hydrazinomethylphosphinate or hydrazinomethylphosphine oxide of claim 1, wherein $R_1$ and $R_2$ are each independently a $C_1$–$C_4$alkyl or $C_1$–$C_4$alkoxy radical, $R_3$ is a chloroacetyl, dichloroacetyl or 2,3,3-trichloroacrylic acid radical, $R_4$ is a hydrogen or a substituent as defined for $R_3$, or is a $C_1$–$C_4$alkyl, $C_2$–$C_4$alkenyl, benzyl, phenethyl, $C_1$–$C_4$alkylcarbonyl, $C_1$–$C_4$alkoxycarbonyl, benzoyl or benzyloxycarbonyl radical and $R_5$ is hydrogen.

* * * * *